US010173950B2

(12) United States Patent
Abudawoud et al.

(10) Patent No.: US 10,173,950 B2
(45) Date of Patent: Jan. 8, 2019

(54) INTEGRATED PROCESS FOR THE PRODUCTION OF BENZENE AND XYLENES FROM HEAVY AROMATICS

(71) Applicant: Saudi Arabian Oil Company, Dhahran (SA)

(72) Inventors: Raed H. Abudawoud, Dhahran (SA); Zhonglin Zhang, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 15/826,117

(22) Filed: Nov. 29, 2017

(65) Prior Publication Data

US 2018/0186710 A1 Jul. 5, 2018

Related U.S. Application Data

(60) Provisional application No. 62/422,124, filed on Jan. 4, 2017.

(51) Int. Cl.
*C07C 4/18* (2006.01)
*C07C 5/10* (2006.01)
(Continued)

(52) U.S. Cl.
CPC ............... *C07C 4/18* (2013.01); *C07C 5/10* (2013.01); *C07C 6/123* (2013.01); *C07C 6/126* (2013.01);
(Continued)

(58) Field of Classification Search
None
See application file for complete search history.

(56) References Cited

U.S. PATENT DOCUMENTS 4,013,734 A 3/1977 Kim
4,053,388 A * 10/1977 Bailey ..................... C07C 15/08
208/89
(Continued)

FOREIGN PATENT DOCUMENTS

EP 0816311 A1 1/1998
WO WO200010944 A1 3/2000
(Continued)

OTHER PUBLICATIONS

Commissaris, Scott E.; "UOP Parex Process", Handbook of Petroleum Refining Processes Third Edition, 2004, chapter 2.6, pp. 2.47-2.53.
(Continued)

*Primary Examiner* — Tam M Nguyen
(74) *Attorney, Agent, or Firm* — Bracewell LLP; Constance G. Rhebergen; Brian H. Tompkins (57) ABSTRACT

Systems and processes for maximizing the production of benzene and para-xylene from heavy reformate are provided. An integrated process and system may include a C9 dealkylation reactor, a transalkylation reactor, and a C10+ dealkylation reactor. The integrated process and system for producing benzene and para-xylene may be configured to additionally produce alkanes in the presence of hydrogen or olefins in the absence of hydrogen. The transalkylation reactor may perform transalkylation of product from the C9 dealkylation reactor and xylene isomerization.

24 Claims, 2 Drawing Sheets

(51) Int. Cl.
| | |
|---|---|
| C07C 13/271 | (2006.01) |
| C07C 15/08 | (2006.01) |
| C07C 15/04 | (2006.01) |
| C07C 15/06 | (2006.01) |
| C07C 15/24 | (2006.01) |
| C07C 6/12 | (2006.01) |
| C10G 63/04 | (2006.01) |
| B01D 53/047 | (2006.01) |

(52) U.S. Cl.
CPC ............ *C07C 13/271* (2013.01); *C07C 15/04* (2013.01); *C07C 15/06* (2013.01); *C07C 15/08* (2013.01); *C07C 15/24* (2013.01); *C10G 63/04* (2013.01); *B01D 53/047* (2013.01); *B01D 2256/16* (2013.01); *B01D 2257/702* (2013.01); *C10G 2300/1096* (2013.01); *C10G 2300/4081* (2013.01); *C10G 2400/20* (2013.01); *C10G 2400/30* (2013.01)

(56) References Cited

U.S. PATENT DOCUMENTS

| | | | |
|---|---|---|---|
| 4,127,471 | A | 11/1978 | Suggitt et al. |
| 4,172,813 | A | 10/1979 | Bertolacini et al. |
| 4,211,886 | A * | 7/1980 | Tabak ................... C07C 4/12 585/321 |
| 4,310,715 | A | 1/1982 | Dorawala et al. |
| 5,004,854 | A | 4/1991 | Yan |
| 5,030,787 | A | 7/1991 | Absil et al. |
| 5,763,720 | A | 6/1998 | Buchanan et al. |
| 5,847,256 | A | 12/1998 | Ichioka et al. |
| 5,866,741 | A | 2/1999 | Wu et al. |
| 5,942,651 | A | 8/1999 | Beech, Jr. et al. |
| 5,952,536 | A | 9/1999 | Nacamuli et al. |
| 6,096,938 | A | 8/2000 | Ghosh |
| 6,204,422 | B1 | 3/2001 | Tsutsui et al. |
| 6,359,184 | B1 | 3/2002 | Kato et al. |
| 6,706,937 | B2 | 3/2004 | Xiao et al. |
| 7,288,687 | B1 | 10/2007 | Frey et al. |
| 7,544,849 | B2 | 6/2009 | Boldingh et al. |
| 7,563,358 | B2 | 7/2009 | Stavens et al. |
| 7,663,010 | B2 | 2/2010 | Levin |
| 7,727,490 | B2 | 6/2010 | Zhou |
| 8,071,828 | B2 | 12/2011 | Cao et al. |
| 8,084,657 | B2 | 12/2011 | Kong et al. |
| 8,183,424 | B2 | 5/2012 | Levin et al. |
| 8,198,502 | B2 | 6/2012 | Bresler et al. |
| 8,431,758 | B2 | 4/2013 | Frey et al. |
| 8,822,747 | B2 | 9/2014 | Corradi et al. |
| 9,000,247 | B2 * | 4/2015 | Abudawoud ............ C07C 4/18 585/319 |
| 9,249,068 | B2 | 2/2016 | Tinger et al. |
| 9,295,970 | B1 | 3/2016 | Tinger et al. |
| 9,302,953 | B2 | 4/2016 | Molinier et al. |
| 9,365,468 | B2 * | 6/2016 | Larson ................... B01J 8/087 |
| 9,469,579 | B2 | 10/2016 | Molinier et al. |
| 2005/0197518 | A1 | 9/2005 | Miller et al. |
| 2007/0203376 | A1 | 8/2007 | Negiz et al. |
| 2008/0021253 | A1 | 1/2008 | Corma Canos et al. |
| 2009/0112034 | A1 | 4/2009 | Levin |
| 2010/0217057 | A1 * | 8/2010 | Domokos ................ B01J 29/40 585/488 |
| 2011/0160489 | A1 * | 6/2011 | Dakka ........................ C07C 2/08 568/338 |
| 2012/0024755 | A1 | 2/2012 | Beech, Jr. et al. |
| 2012/0083638 | A1 | 4/2012 | Boldingh et al. |
| 2013/0165719 | A1 | 6/2013 | Negiz et al. |
| 2014/0100402 | A1 | 4/2014 | Gawlik et al. |
| 2015/0094508 | A1 | 4/2015 | Corradi et al. |
| 2015/0166435 | A1 | 6/2015 | Serban et al. |
| 2016/0031771 | A1 * | 2/2016 | Nubel ................... C07C 5/2737 585/254 |
| 2016/0185686 | A1 | 6/2016 | Molinier et al. |

FOREIGN PATENT DOCUMENTS

| | | |
|---|---|---|
| WO | 2004056945 A1 | 7/2004 |
| WO | 2007137017 A1 | 11/2007 |
| WO | WO2012006039 A2 | 1/2012 |
| WO | WO2013158956 A1 | 10/2013 |

OTHER PUBLICATIONS

International Search Report and the Written Opinion for International Application No. PCT/US2013/037304 (SA5038/PCT) dated Jul. 4, 2013; pp. 1-9.

Johnson, James A.; "Aromatics Complexes", Handbook of Petroleum Refining Processes Third Edition, 2004, chapter 2.1, pp. 2.3-2.11.

Niegiz, Antoine and Stoodt, Thomas J.; "UOP Tatoray Process", Handbook of Petroleum Refining Processes Third Edition, 2004, Chapter 2.7, pp. 2.55-2.63.

Silady, Ptrick J.; "UOP Isomar Process", Handbook of Petroleum Refining Processes Third Edition, 2004, Chapter 2.5, pp. 2.39-2.46.

International Search Report and Written Opinion for International Application No. PCT/US2018/012129 (SA5565); International Filing Date Jan. 3, 2018; dated Apr. 24, 2018 (pp. 1-14).

Alario, et al., "Para-xylene Manufacturing: Catalytic Reactions and Processes," 3 Catalytic Science Series: Zeolites for Cleaner Technologies (2002), 189-207.

International Search Report and Written Opinion for International Application No. PCT/US2018/032874 (SA5633); dated Jul. 5, 2018; 13 pgs.

* cited by examiner

INTEGRATED PROCESS FOR THE PRODUCTION OF BENZENE AND XYLENES FROM HEAVY AROMATICS

CROSS-REFERENCE TO RELATED APPLICATIONS

This application claims priority from U.S. Provisional Application No. 62/442,124 filed Jan. 4, 2017, and titled "INTEGRATED PROCESS FOR THE PRODUCTION OF BENZENE AND XYLENES FROM HEAVY AROMATICS." For purposes of United States patent practice, this application incorporates the contents of the Provisional application by reference in its entirety.

BACKGROUND

Field of the Disclosure

The present disclosure generally relates to the processing of heavy reformate. More specifically, embodiments of the disclosure relate to the production of para-xylene and benzene from heavy reformate.

Description of the Related Art

Petrochemical refiners are facing issues with utilization of heavy reformate streams. Environmental regulations by governments and regions around the world are limiting the amount of aromatics (C6+) content in gasoline fuel. Gasoline refiners and blenders traditionally use C6+ aromatics, which include the C6-8 BTEX components (benzene, toluene, ethylbenzene, and xylenes), to improve octane ratings and anti-knocking attributes of motor fuels Although motor fuel use is a major consumer of BTEX components, each of the BTEX products has alternative markets for their use besides motor fuels. Benzene is a widely used precursor for many chemical and solvation processes. Toluene and ethylbenzene are also reactants and precursors in chemical and polymerization processes. The three isomers of xylene ($C_8H_{10}$)—para-xylene (p-xylene), meta-xylene (m-xylene), and ortho-xylene (o-xylene)—are all petrochemical feedstocks of value. When mixed xylenes form during catalytic reformation, the less commercially valuable m-xylene forms in greater amounts than either p- or o-xylenes because of thermodynamic equilibrium relationships between the three isomers. Market demand, however, currently favors p-xylene followed distantly by o-xylene.

Reformate, the bottoms product from naphtha catalytic reforming, and pyrolysis gasoline ("pygas"), a byproduct of ethylene cracking, are the usual sources for these compounds. Extracting the valuable BTEX components from reformate and pygas leaves a heavy reformate, which includes mainly C9+ alkyl aromatic compounds (pygas may also contain diolefins if not previously separated). Heavy reformate can also form from running these processes at higher severity (that is, temperatures) to produce more hydrogen, alkanes and olefins from naphtha.

SUMMARY

Conventional processing of aromatics includes the extraction of benzene, toluene, and xylene (BTX) from heavy reformate (such as catalytic naphtha reformate) or stream cracker pyrolysis gasoline. The remaining C9+ fraction from the BTX extraction is partially sent to transalkylation to produce additional BTX, and the heavier portion of C9+ aromatics, such as C10+ aromatics, are rejected. The extracted xylenes from the BTX extraction are typically directed to a para-xylene separation step (either adsorption or crystallization out of the mixed xylenes stream), after which the remaining xylene isomers and ethylbenzene are sent to a stand-alone xylene isomerization reactor to re-establish the thermodynamic equilibrium of xylenes and form para-xylene in the process. Benzene is typically produced via the extraction process and may be produced with xylene via toluene disproportionation, thermal dealkylation, or hydrodealkylation. Thus, the conventional processing of aromatics typically includes a stand-alone xylene isomerization reactor and a rejection of C10+ aromatics or the dealkylation of toluene to form benzene in a dedicated reaction. Such conventional processing may also include feeding fresh or reformate-extracted toluene to the C9 transalkylation process (for example, adding fresh toluene to optimize xylene yield).

Advantageously, embodiments of the disclosure use all aromatic hydrocarbons (including C10+ aromatics) to maximize production of benzene and para-xylene. Further, embodiments of the disclosure advantageously enable the production of olefins instead of alkanes by changing the processing conditions and configuration of the dealkylation reactors, transalkylation reactor, or both. Further, embodiments the disclosure minimize the reaction steps used to produce benzene and para-xylene, such as by combining C9 transalkylation and xylene isomerization in one reactor (that is, one process stage).

In one embodiment, a heavy reformate processing system for producing benzene and para-xylene from a heavy reformate is provided. The system includes a reformate splitter operable to receive a feed stream. The feed stream includes heavy reformate, and the reformate splitter is further operable to produce benzene, toluene, and a C8+ aromatics product. The C8+ aromatics product is provided to a xylene splitter. The system further includes a para-xylene separator operable to receive a C8 aromatic product from the xylene splitter and produce a first xylene product that includes para-xylene and a second xylene product that includes ortho-xylene and meta-xylene. The system also includes a first dealkylation reactor operable to receive a C10+ aromatics product from the xylene splitter and produce the first dealkylation product. The first dealkylation reactor is further operable to produce alkanes from the C10+ aromatics product and hydrogen or produce olefins from the C10+ aromatic product in the absence of hydrogen. The system also includes a second dealkylation reactor operable to receive a C9 aromatics product from the xylene separator and produce a second dealkylation product. The second dealkylation reactor is further operable to produce alkanes from the C9 aromatics product and hydrogen and produce olefins from the C9 aromatic product in the absence of hydrogen. The system further includes a transalkylation reactor operable to receive the second dealkylation product from the second dealkylation reactor and produce the transalkylation product. The transalkylation reactor is further operable to produce alkanes from the second dealkylation product and hydrogen or produce olefins from the second dealkylation product in the absence of hydrogen.

In some embodiments, the feed stream includes the transalkylation product and the first dealkylation product. In some embodiments, the transalkylation reactor is further operable to perform isomerization of xylene to promote the formation of para-xylene. In some embodiments, the system includes a pressure swing adsorption (PSA) unit operable to receive alkanes and unreacted hydrogen from the first dealkylation reactor, the second dealkylation reactor, and the transalkylation reactor. In some embodiments, the first dealkylation reactor is further operable to receive recovered hydrogen from the PSA unit. In some embodiments, the transalkylation reactor is further operable to receive recovered hydrogen from the PSA unit. In some embodiments, the system includes a C9/C10+ splitter downstream from the transalkylation reactor. The C9/C10+ splitter is operable to receive a portion of the transalkylation product from the transalkylation reactor and produce a C9 aromatics stream and a C10+ aromatics stream. In some embodiments, the transalkylation reactor is further operable to receive the C9 aromatics stream produced by the C9/C10+ splitter. In some embodiments, the first dealkylation reactor is further operable to receive the C10+ aromatics stream produced by the C9/C10+ splitter. In some embodiments, the transalkylation reactor is further operable to receive toluene produced by the reformate splitter. In some embodiments, the second dealkylation reactor operable is further operable to receive the second xylene product that includes ortho-xylene and meta-xylene produced by the xylene splitter. In some embodiments, the alkanes include ethane and propane. In some embodiments, the olefins include ethylene and propylene.

In another embodiment, a method for producing benzene and para-xylene from a heavy reformate is provided. The method includes receiving a feed stream at a reformate splitter. The feed stream includes heavy reformate and operating the reformate splitter to produce benzene, toluene, and C8+ aromatics from the feed stream. The method also includes operating a xylene splitter to receive the C8+ aromatics and produce C8 aromatics, C9 aromatics, and C10+ aromatics and operating a para-xylene separator to receive the C8 aromatics from the xylene splitter and produce a first xylene product that includes para-xylene and a second xylene product that includes ortho-xylene and meta-xylene. The method further includes operating a first dealkylation reactor to receive the C10+ aromatics from the xylene separator and produce the first dealkylation product, operating a second dealkylation reactor operable to receive the C9 aromatics from the xylene separator and produce a second dealkylation product, and operating a transalkylation reactor to receive the second dealkylation product from the second dealkylation reactor and produce the transalkylation product.

In some embodiments, the method includes operating the first dealkylation reactor to produce alkanes from the C10+ aromatics product and hydrogen, operating the second dealkylation reactor to produce alkanes from the C9 aromatics product and hydrogen, and operating the transalkylation reactor to produce alkanes from the second dealkylation product and hydrogen. In some embodiments, the alkanes include ethane and propane. In some embodiments, the method includes operating a pressure swing adsorption (PSA) unit to receive alkanes and unreacted hydrogen from the first dealkylation reactor, the second dealkylation reactor, and the transalkylation reactor. In some embodiments, the method includes operating a C9/C10+ splitter downstream from the transalkylation reactor to receive a portion of the transalkylation product from the transalkylation reactor and produce a C9 aromatics stream and a C10+ aromatics stream. In some embodiments, the method includes operating the transalkylation reactor to receive the C9 aromatics stream produced by the C9/C10+ splitter. In some embodiments, the method includes operating the first dealkylation reactor to receive the C10+ aromatics stream produced by the C9/C10+ splitter. In some embodiments, the method also includes operating the second dealkylation reactor operable is further operable to receive the second xylene product that includes ortho-xylene and meta-xylene produced by the xylene splitter. In some embodiments, the method further includes operating the first dealkylation reactor to produce olefins from the C10+ aromatic product in the absence of hydrogen, operating the second dealkylation reactor to produce olefins from the C9 aromatic product in the absence of hydrogen, and operating the transalkylation reactor to produce olefins from the second dealkylation product in the absence of hydrogen. In some embodiments, the olefins include ethylene and propylene. In some embodiments, the method includes operating transalkylation reactor to perform isomerization of xylene to promote the formation of para-xylene.

In another embodiment, a reformate processing system for producing benzene and para-xylene from a heavy reformate containing methyl ethyl benzenes and tri-methyl benzenes is provided. The method includes a first dealkylation reactor operable to receive a C10+ aromatics product separated from a heavy reformate feed. The first dealkylation reactor is operable to produce a first dealkylation product that includes benzene. In some embodiments, the system includes a second dealkylation reactor operable to receive a C9 aromatics product separated from a heavy reformate feed. The second dealkylation reactor is operable to produce a second dealkylation product that includes benzene and toluene. In some embodiments, the system includes a transalkylation reactor operable to receive the second dealkylation product from the second dealkylation reactor and produce a transalkylation product that includes benzene, toluene, and xylene. The transalkylation reactor is further operable to receive a mixed xylene feed and perform isomerization of xylene.

In some embodiments, the first dealkylation reactor is further operable to produce alkanes from the C10+ aromatics product and hydrogen, the second dealkylation reactor is further operable to produce alkanes from the C9 aromatics product and hydrogen, and the transalkylation reactor is further operable to produce alkanes from the second dealkylation product and hydrogen. In some embodiments, the first dealkylation reactor is further operable to produce olefins from the C10+ aromatics product in the absence of hydrogen, the second dealkylation reactor is further operable to produce olefins from the C9 aromatics product in the absence of hydrogen, and the transalkylation reactor is further operable to produce olefins from the second dealkylation product in the absence of hydrogen.

DETAILED DESCRIPTION

The present disclosure will now be described more fully with reference to the accompanying drawings, which illustrate embodiments of the disclosure. This disclosure may, however, be embodied in many different forms and should not be construed as limited to the illustrated embodiments. Rather, these embodiments are provided so that this disclosure will be thorough and complete, and will fully convey the scope of the disclosure to those skilled in the art.

Embodiments of the disclosure include systems and processes for maximizing the production of benzene and para-xylene from heavy reformate. Such integrated processes and systems for producing benzene and para-xylene from heavy reformate may include three reactors (also referred to as "stages"): a C9 dealkylation reactor, a transalkylation/isomerization reactor (that is, a reactor that operates to provide both transalkylation and isomerization reactions), and a C10+ dealkylation reactor. In some embodiments, C9 aromatics (for example, trimethylbenzene (TMB)) and hydrogen may be provided to the C9 dealkylation reactor to produce toluene, unconverted C9 aromatics, and light gases (for example, light alkanes such as ethane and propane, and unreacted hydrogen). The toluene and unconverted C9 aromatics from the C9 dealkylation reactor and hydrogen may be provided to the transalkylation/isomerization reactor to produce BTX, C9 aromatics, C10+ aromatics, and light gases (for example, light alkanes and unreacted hydrogen), under reaction conditions for the maximization of xylene production. In some embodiments, the transalkylation/isomerization reactor may also isomerize para-xylene-free mixed xylenes received from a para-xylene separator to reestablish the thermodynamic equilibrium of C8 aromatics (that is, xylene isomers) para-xylene. C10+ aromatics and hydrogen may be provided to the C10+ dealkylation reactor to produce BTX, C9 aromatics, unconverted C10+ aromatics, and light gases (for example, light alkanes and unreacted hydrogen). The light gases (for example, light alkanes and unreacted hydrogen) produced from the C9 dealkylation reactor, the transalkylation/isomerization reactor, and the C10+ dealkylation reactor are provided to a pressure swing adsorption (PSA) unit for the recovery of hydrogen and the recycling of recovered hydrogen to the reactors. The BTX from the transalkylation/isomerization reactor, and the C10+ dealkylation reactor may be recycled to a reformate splitter to recover benzene and toluene, and then para-xylene recovery from a downstream para-xylene separator.

In some embodiments, an integrated process and system for producing benzene and para-xylene from heavy reformate using the three reactors (or "stages") described in the disclosure may be configured to produce olefins instead of alkanes. In such embodiments, the C9 dealkylation reactor, the transalkylation/isomerization reactor, and the C10+ dealkylation reactor may be operated in the absence of hydrogen to produce olefins instead of alkanes and unrecovered hydrogen. For example, in such embodiments, C9 aromatics (for example, TMB) may be provided to the C9 dealkylation reactor to produce toluene, unconverted C9 aromatics, and olefins (for example, light olefins such as ethylene and propylene). The toluene and unconverted C9 aromatics from the C9 dealkylation reactor may be provided to the transalkylation/isomerization reactor to produce BTX, C9 aromatics, C10+ aromatics, and olefins, under reaction conditions for the maximization of xylene production. C10+ aromatics may be provided to the C10+ dealkylation reactor to produce BTX, C9 aromatics, unconverted C10+ aromatics, and olefins. In such embodiments, the dealkylation reactors may be configured with appropriate catalysts for operation without hydrogen and the production of olefins. Moreover, in such embodiments, the integrated process and system may omit a PSA unit and the recovery of hydrogen.

The continuous removal of C10+ aromatics from the C9 dealkylation and transalkylation processes for processing in the C10+ dealkylation reactor increases the lifetime of the C9 dealkylation and transalkylation catalysts due the absence of coke precursors. Additionally, the C10+ dealkylation reactor may be configured to enable the production of BTX. In such embodiments, toluene may be separated from the BTX and provided to the transalkylation/isomerization reactor. Further, xylene isomerization is performed in the transalkylation/isomerization reactor, eliminating separate transalkylation reactors. Consequently, C9+ aromatics may be completely utilized to produce benzene and mixed xylenes via the C9 dealkylation and transalkylation processes and the C10+ dealkylation process.

As used in the disclosure the term "mixed xylenes" refers to a mixture of all three xylene isomers: para-xylene, ortho-xylene, and meta-xylene. As used in the disclosure, the term "para-xylene-free mixed xylenes" refers to a mixture of the two xylene isomers of ortho-xylene and meta-xylene.

In some embodiments, the operating conditions of the C10+ dealkylation reactor described in the disclosure may be varied to influence the composition of product (for example, to maximize xylene production from C10+ aromatics). An example C10+ aromatic stream that may be provided to the C10+ dealkylation reactor described supra is shown in Table 1:

TABLE 1

Composition of Example C10+ aromatics stream

| Compound | Composition (weight of the total weight (wt %)) |
|---|---|
| 1,2-dimethyl-4-ethylbenzene | 10-20 |
| 1,2,3,5-tetramethylbenzene | 10-20 |
| 1,2,4,5-tetramethylbenzene | 5-15 |
| 1,3-dimethyl-4-ethylbenzene | 2-10 |
| 1,3-dimethyl-5-ethylbenzene | 2-10 |
| 1,4-dimethyl-2-ethylbenzene | 2-10 |
| 1-methyl-3-propylbenzene | 2-10 |
| naphthalene | <10 |
| 1,4-diethylbenzene | 1-5 |
| 1,2,3-trimethylbenzene | 1-5 |
| 1-methyl-4-propylbenzene | 1-5 |
| 1,2,4-trimethylbenzene | <2 |
| 2-methylnaphthalene | <2 |
| 1,3-diethylbenzene | <2 |
| Total | 100 |

Figure 2:
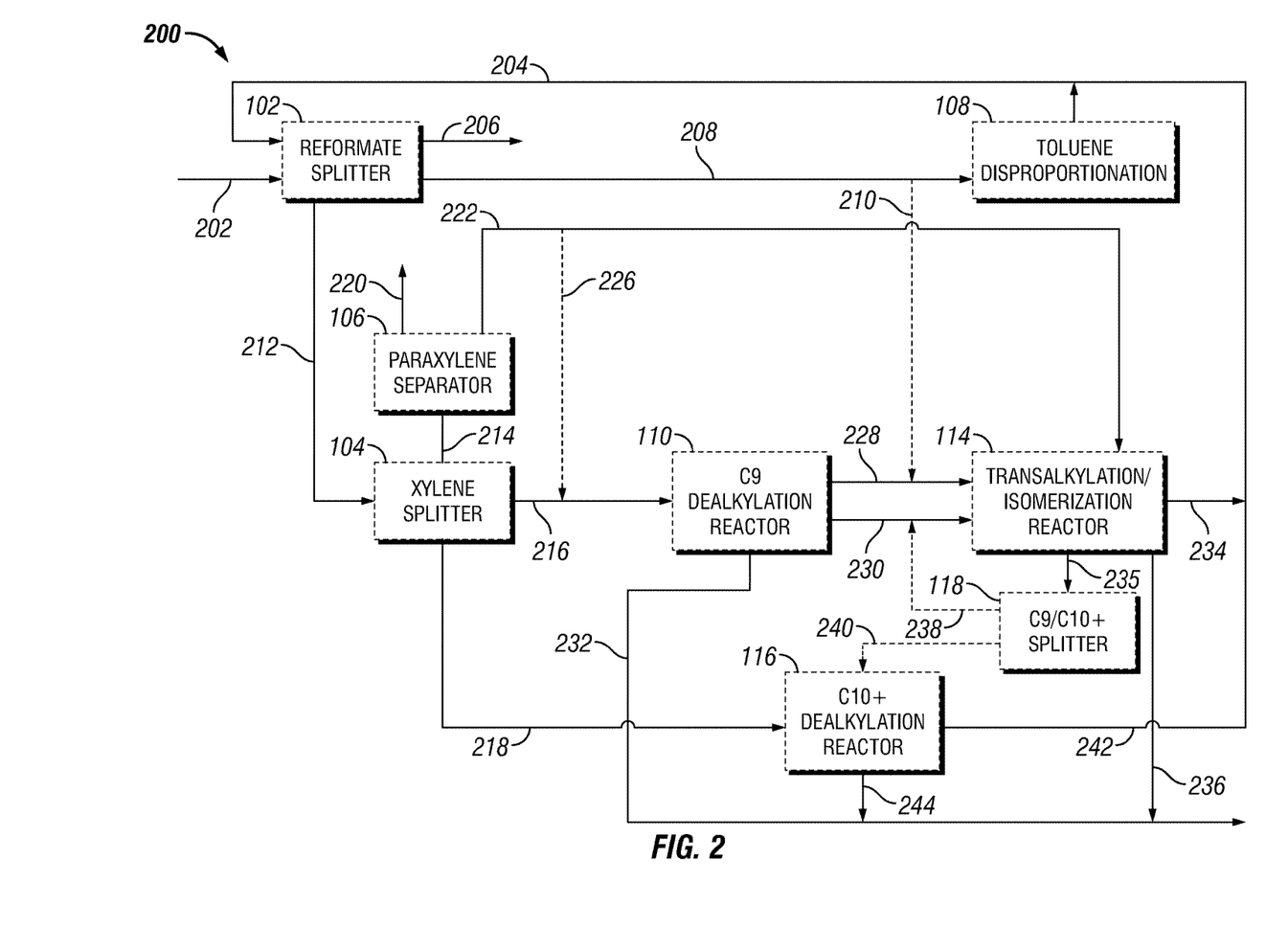
FIG. 2 is a process flow diagram for a dealkylation-transalkylation process for producing benzene and para-xylene from heavy reformate in accordance with another embodiment of the disclosure.

As shown in Table 1, dimethylethylbenzenes (DMEBs) are the most abundant compounds of the example C10+ aromatics stream and range between 16 wt % and 50 wt %. The next most abundant compounds are tetramethylbenzenes that range between 15 wt % and 35 wt %. Accordingly, the operating conditions and reaction extent of the C10+ dealkylation reactor can be varied to maximize benzene production or xylene production, depending on how many alkyl groups are removed during the dealkylation reaction. Additionally, the large number of ethyl and, in smaller numbers, propyl groups attached to the C10+ aromatic molecules may easily form olefins such as ethylene and propylene when the dealkylation reaction is performed in the absence of hydrogen, as illustrated in FIG. 2 and described further infra.

Advantageously, the addition of the C10+ dealkylation reactor may increase the yield of mixed xylenes over prior art processes without a C10+ dealkylation reactor. The addition of the C10+ dealkylation reactor may also similarly increase the yield of benzene over prior art processes without a C10+ dealkylation reactor. Table 2 depicts products from an example benzene and xylene production process without a C10+ dealkylation reactor ("Case 1") and an example benzene and xylene production process with a C10+ dealkylation reactor ("Case 2"), based on a charge feed of 380 kilotons per annum (KTA) of heavy reformate and with product flowrate expressed in tons per year:

TABLE 2

Yields from Example Processes with and without a C10+ dealkylation reactor

| Product | Case 1 (without C10+ dealkylation reactor) Flowrate (tons per year) | Case 2 (with C10+ dealkylation reactor Flowrate (tons per year) |
|---|---|---|
| Mixed Xylene | 177,271 | 281,004 |
| Benzene | 10,353 | 20,064 |
| Light Ends | 22,576 | 49,407 |
| Fuel Gas | 11,147 | 44,280 |
| C10+ Aromatics | 162,153 | |
| Total | 383,500 | 394,755 |

As shown in Table 2, the mixed xylene yield and benzene yield increased after the addition of a C10+ dealkylation reactor.

Production of Benzene, Para-Xylene, and Alkanes

Figure 1:
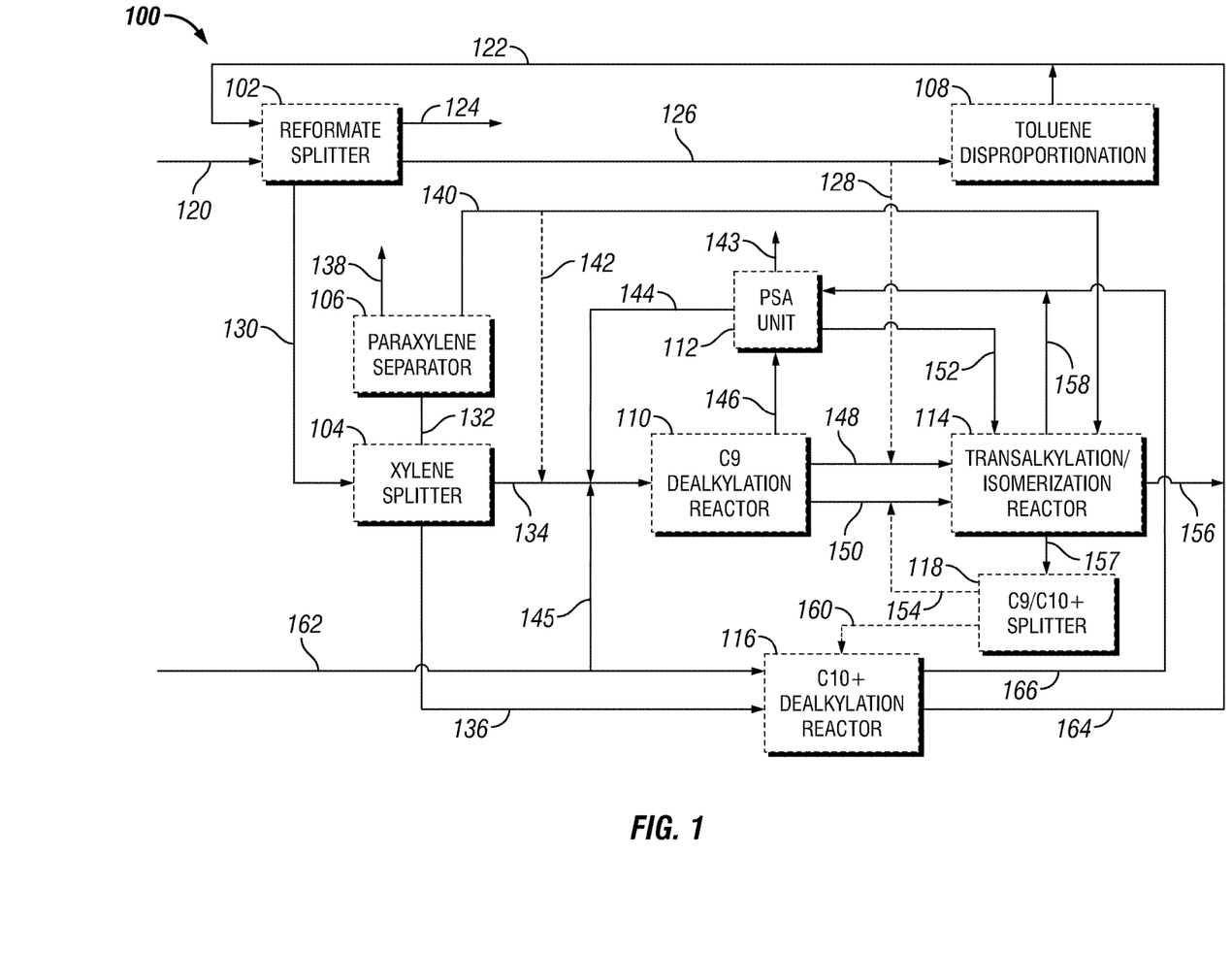
FIG. 1 is a process flow diagram for a dealkylation-transalkylation process for producing benzene and para-xylene from heavy reformate in accordance with an embodiment of the disclosure.

FIG. 1 depicts an integrated process 100 for an embodiment of the three reactor dealkylation and transalkylation system for the production of benzene and para-xylene from heavy reformate in accordance with an embodiment of the disclosure. As shown in FIG. 1, the process 100 includes a reformate splitter 102, a xylene splitter 104, a para-xylene separator 106, and a xylene and a toluene disproportionation unit 108. The process 100 shown in FIG. 1 also includes a C9 dealkylation reactor 110, a pressure swing adsorption (PSA) unit 112, a transalkylation/isomerization reactor 114, and a C10+ dealkylation reactor 116. In some embodiments, the process 100 may include a C9/C10+ splitter 118 downstream of the transalkylation/isomerization reactor 114. As described infra, the process 100 includes three reactors to process a reformate feed and produce benzene, para-xylene, and alkanes from the reformate feed: the C9 dealkylation reactor 110, the transalkylation/isomerization reactor 114, and the C10+ dealkylation reactor 116.

The process 100 includes separate processing of C10+ aromatics in the C10+ dealkylation reactor 116 and avoids rejection of C10+ aromatics. Further, the separate processing of C10+ aromatics removes the C10+ aromatics from the C9 dealkylation and transalkylation processes and the respective reactors 110 and 114, thus enabling a reduction in the reactor size of the C9 dealkylation reactor 110 and the transalkylation/isomerization reactor 114. Additionally, the xylene isomerization and transalkylation processes are conducted in the transalkylation/isomerization reactor 114, thus eliminating a separate isomerization reactor. Further, in some embodiments, TMB-rich C9 aromatics produced by the transalkylation/isomerization reactor 114 and separated by the C9/C10+ splitter 118 may be recycled to the inlet of the transalkylation/isomerization reactor 114, enabling further reduction of the reactor size of the C9 dealkylation reactor 110.

As shown in FIG. 1, a feed stream 120 of the process 100 may be a combined stream of reformate from a typical catalytic naphtha reformer and a recycled product stream 122 from the transalkylation/isomerization reactor 114 and the C10+ dealkylation reactor 116. In other embodiments, the feed stream 120 may be a combined stream of pyrolysis gasoline from a steam cracking furnace and the recycled product stream 122 from the transalkylation/isomerization reactor 114 and the C10+ dealkylation reactor 116.

As shown in FIG. 1, the feed stream 120 is provided to the reformate splitter 102. The reformate splitter 102 may separate and produce product streams of benzene 124 and toluene 126 from the feed stream 120. As will be appreciated, the reformate splitter 102 may include suitable separation processes for extracting benzene and toluene from the feed stream 120. For example, the reformate splitter 102 may include the extraction of benzene using solvent extraction and the separation of toluene using a fractionation column. The toluene stream 126 output from the reformate splitter 102 may be provided to the toluene disproportionation unit 108. The toluene disproportionation unit 108 may convert the toluene stream 126 to benzene and xylene which, in some embodiments, may be provided to the reformate splitter 102 (for example, as shown by recycled product stream 204). In some embodiments, a portion 128 of the toluene output from the reformate splitter 102 may be provided to the transalkylation/isomerization reactor 114, as described further infra, to improve transalkylation efficiency. The reformate splitter 102 may also remove saturated liquid hydrocarbons (for example, napthenes and paraffins). The C8+ aromatics 130 output from the reformate splitter 102 may be provided to the xylene splitter 104.

The xylene splitter 104 may separate C8 aromatics 132 (for example (xylenes and ethylbenzene), C9 aromatics 134, and C10+ aromatics from the C8+ aromatics stream 130 received from the reformate splitter 102. For example, the xylene splitter may separate C8 aromatics 132 from the tops of the columns, C9 aromatics 134 from the side stream of the columns, and C10+ aromatics 136 from the bottoms of the columns. As shown in FIG. 1, the C8 aromatics 132 may be provided to the para-xylene separator 106, the C9 aromatics 134 may be provided to the C9 dealkylation reactor 110, and the C10+ aromatics 136 may be provided to the C10+ dealkylation reactor 116.

The para-xylene separator 106 may separate and produce product streams of para-xylene 138 and para-xylene-free mixed xylenes 140 (that is, ortho- and meta-xylenes) from the C8 aromatics stream 132 received from the reformate splitter 102. In some embodiments, the para-xylene separator 106 may be an adsorptive process or a crystallization process. In some embodiments, the para-xylene-free mixed xylenes stream 140 produced by the para-xylene separator 106 may be provided to the transalkylation/isomerization reactor 114 for reestablishing a C8 aromatics thermodynamic equilibrium of xylene isomers and promoting formation of additional para-xylene. Additionally or alternatively, a portion 142 (or, in some embodiments, all of) of the para-xylene-free mixed xylenes stream 140 may be provided to the C9 dealkylation reactor 110 for subsequent isomerization over a catalyst (for example, a narrower pore catalyst) that may be more suitable for the isomerization of xylenes.

As described infra, the PSA unit 112 may receive light gases (for example, light alkanes and unreacted hydrogen) from the C9 dealkylation reactor 110, the transalkylation/isomerization reactor 114, and the C10+ dealkylation reactor 116. The PSA unit 112 may recover hydrogen from the light gases for further use by the reactors to minimize additional hydrogen requirements. The PSA unit 112 may also produce a product stream of hydrogen-free gases 143 (that is, the alkanes produced from the reactors 110, 114, and 116) that may be purged or recovered for use as a heating source.

As shown in FIG. 1 and as previously discussed, the C9 dealkylation reactor 110 may receive the C9 aromatics 134 from the xylene splitter 104 and produce product streams of toluene 148, unconverted C9 aromatics 150, and light gases 146 (for example, light alkanes such as ethane and propane, and unreacted hydrogen). As also shown in FIG. 1, the C9 dealkylation reactor 110 may receive a hydrogen stream 144 of hydrogen recovered by and output from the PSA unit 112. In some embodiments, the C9 dealkylation reactor 110 may receive additional hydrogen 145 from a hydrogen source. In some embodiments, as noted supra, the C9 dealkylation reactor 110 may receive a portion 142 (or, in some embodiments, all of) of the para-xylene-free mixed xylenes stream 140 output from the para-xylene separator 106. The C9 dealkylation reactor 110 may be configured to achieve reaction conditions sufficient to maximize the conversion of C9 aromatics rich in methylethylbenzenes (MEBs), such as, ethyltoluenes, isobenzenes, and propylbenzenes, to toluene, benzene, and alkanes (for example, ethane and propane).

The light gases stream 146 produced by the C9 dealkylation reactor 110 may be provided to the PSA unit 112. The PSA unit 112 may separate and produce a product stream of hydrogen from the light gases 146 and, as previously mentioned, the hydrogen stream 144 may be recycled to the C9 dealkylation reactor 110. In some embodiments, the C9 dealkylation reactor 110 may be operated under the following conditions: a temperature in the range of about 200° C. to about 540° C., pressure in the range of about 10 bar to about 50 bar, liquid hourly velocity in the range of about 1 $hr^{-1}$ to about 20 $hr^{-1}$, and a hydrogen to feed stream ratio in the range of 0 to 4.

In some embodiments, the catalysts used in the C9 dealkylation reactor 110 for hydrodealkylation with hydrogen may include bifunctional catalysts. The hydrodealkylation catalyst used in the C9 dealkylation reactor 110 may be capable of selectively converting MEBs and hydrogen into toluene, benzene and alkanes. In some embodiments, the hydrodealkylation catalyst may be capable of converting a significant portion and, in some embodiments, all of the MEBs to toluene, benzene, and alkanes at the appropriate reaction operating conditions. It should be appreciated that one of ordinary skill in the art may select an appropriate, commercially available hydrodealkylation catalyst for performing the dealkylation portion of the process without undue or excessive experimentation. As will be appreciated, such parameters in selecting the physical, selectivity, and activity attributes of an appropriate hydrodealkylation catalyst may include dealkylation stage operating conditions, feed stock compositions, ratios of hydrogen to MEBs, desired conversion efficacy and efficiency, dealkylation stage residence time, and physical attributes of the dealkylation stage. In some embodiments, the catalyst used in the C9 dealkylation reactor 110 may include a fluorinated zeolite catalyst. In some embodiments, the zeolite catalyst may include metal ions (for example, $Ni^{2+}$) incorporated into the crystalline structure of the catalyst. In some embodiments, the metal ions may include other Group 8, Group 9, and Group 10 transition metals, such as cobalt and palladium.

In some embodiments, the catalysts used to conduct dealkylation in the C9 dealkylation reactor 110 may also be capable of conducting xylene isomerization in embodiments in which the portion 142 (or, in some embodiments, all of) of the para-xylene-free mixed xylenes stream 140 from the para-xylene separator 106 is provided to the C9 dealkylation reactor 110. The toluene stream 148 and unconverted C9 aromatics stream 150 produced by the C9 dealkylation reactor 110 may be provided to the downstream transalkylation/isomerization reactor 114. In some embodiments, any benzene formed by the C9 dealkylation reactor 110 may also be provided to the transalkylation/isomerization reactor 114 with these product streams.

The transalkylation/isomerization reactor 114 may receive the liquid effluent (that is, the toluene stream 148 and the unconverted C9 aromatics stream 150) from the C9 dealkylation reactor 110 and produce product streams of BTX and C9+ aromatics 156 and light gases 158 (that is, light alkanes and unreacted hydrogen). As shown in FIG. 1, the transalkylation/isomerization reactor 114 may also receive a hydrogen 152 stream produced by the PSA unit 112, and the para-xylene-free mixed xylenes stream 140 produced by the para-xylene separator 106. As also shown in FIG. 1, in some embodiments, the transalkylation/isomerization reactor 114 may also receive the portion 128 of toluene from the reformate splitter 102. In some embodiments that include the C9/C10+ splitter 118, the transalkylation/isomerization reactor 114 may receive a recycled C9 aromatics stream 154 produced by the C9/C10+ splitter 118

The transalkylation/isomerization reactor 114 may be configured to maximize the transalkylation of unconverted TMB-rich C9 aromatics and toluene to produce xylenes. The transalkylation/isomerization reactor 114 may also be configured to perform isomerization of the para-xylene-free mixed xylenes stream 140 to reestablish the C8 aromatics thermodynamics equilibrium and promote production of para-xylene. The light gases stream 158 produced by the transalkylation/isomerization reactor 114 may be provided to the PSA unit 112 for recovery of hydrogen, as described supra. In some embodiments, the transalkylation/isomerization reactor 114 may be operated under the following conditions: a temperature in the range of about 200° C. to about 540° C., pressure in the range of about 10 bar to about 50 bar, liquid hourly velocity in the range of about 1 $hr^{-1}$ to about 20 $hr^{-1}$, and a hydrogen to feed stream ratio in the range of 0 to 4.

The transalkylation catalyst used in the transalkylation/isomerization reactor 114 may be capable of selectively converting TMBs and toluene into mixed xylenes. In some embodiments, the transalkylation catalyst used in the transalkylation/isomerization reactor 114 may be capable of converting a significant portion and, in some embodiments, all, of the TMBs in the C9 aromatics stream to mixed xylenes in the presence of appropriate reaction operating conditions. It should be appreciated that one of ordinary skill in the art may select an appropriate, commercially available transalkylation catalyst for performing the transalkylation portion of the process without undue or excessive experimentation. As will be appreciated, such parameters in selecting the physical, selectivity, and activity attributes of an appropriate transalkylation catalyst may include transalkylation operating conditions, feed stock compositions, ratios of toluene to TMBs, desired conversion efficacy and efficiency, stage residence time, and physical attributes of the second stage reaction vessel to support the conversion of TMBs and toluene to mixed xylenes using a transalkylation catalyst. In some embodiments, the catalyst used in the transalkylation/isomerization reactor 114 may include a beta zeolite having an activity promoter selected from the group consisting of silicon, phosphorus, boron, magnesium, tin, titanium, zirconium, molybdenum, germanium, indium, lanthanum, cesium, and any oxide thereof.

As shown in FIG. 1, in some embodiments, the BTX and C9+ aromatics stream 156 produced by the transalkylation/isomerization reactor 114 may be recycled to the reformate splitter 102 for the recovery of benzene and toluene and subsequent recovery of para-xylene via the para-xylene separator 106. In other embodiments, the process 100 may include may include the C9/C10+ splitter 118 downstream from the transalkylation/isomerization reactor 114. In such embodiments, a portion 157 of the BTX and C9+ aromatics stream produced by the transalkylation/isomerization reactor 114 may be provided to the C9/C10+ splitter 118. For example, in some embodiments, the C9/C10+ splitter 118 may be included when reaction conditions in the transalkylation/isomerization reactor 114 result in TMBs as the majority of C9 aromatics produced by the transalkylation/isomerization reactor 114. The C9/C10+ splitter 118 may separate C9 aromatics from C10+ aromatics and produce product streams of C9 aromatics 154 and C10+ aromatics 160. In such embodiments, the C9 aromatics stream 154 produced by the C9/C10+ splitter 118 may be recycled to the transalkylation/isomerization reactor 114, and the C10+ aromatics stream 160 produced by the C9/C10+ splitter 118 may be provided to the C10+ dealkylation reactor 116.

As shown in FIG. 1, the C10+ dealkylation reactor 116 may receive the C10+ aromatics stream 136 from the xylene splitter 104 and a hydrogen stream 162 and produce product streams of BTX, C9 aromatics, and unconverted C10 aromatics 164 and light gases 166 (that is, light alkanes and unrecovered hydrogen). In alternate embodiments, the C10+ dealkylation reactor 116 may receive steam from a steam source and may implement a steam dealkylation process. In embodiments of the process 100 that include the C9/C10+ splitter 118, the C10+ dealkylation reactor 116 may also receive the C10+ aromatics stream 160 from the C9/C10+ splitter 118. The C10+ dealkylation reactor 116 may be configured to remove alkyl groups attached to aromatic benzene rings to produce a benzene-rich product stream. For example, compounds with two aromatic rings, such as naphthalene, have one of the rings saturate and crack to produce light gases and benzene. The BTX, C9 aromatics, and unconverted C10 aromatics stream 164 produced by the C10+ dealkylation reactor 116 may be recycled to the reformate splitter 102 for the recovery of benzene and toluene and subsequent recovery of para-xylene via the para-xylene separator 106. The light gases stream 166 produced by the C10+ dealkylation reactor 116 may be provided to the PSA unit 112 for hydrogen recovery. In some embodiments, the C10+ dealkylation reactor 116 may be operated under the following conditions: temperature in the range of about 300° C. to about 450° C., pressure in the range of about 10 bar to about 40 bar, weight hour space velocity (WHSV) in the range of about 0.5 to about 3, and a hydrogen to feed stream ratio in the range of 2 to 4. In some embodiments, the C10+ dealkylation reactor 116 may implement a steam dealkylation process and may be operated using steam and a steam dealkylation catalyst under the following conditions and procedure: initially operating at temperature in the range of about 315° C. to about 510° C. for a time period in the range of about 30 to about 180 seconds, during which time the activity of the steam dealkylation catalyst may decrease to less than about 90% of the initial activity as measured by the mole percent conversion of feed aromatics to dealkylate product; interrupting the flow of feed aromatics when the activity of the steam dealkylation catalyst has decreased to less than about 90%; and contacting the steam dealkylation catalyst with steam at a temperature in the range of about 315° C. to about 510° C. to regenerate the catalyst to about 75% of its initial activity and recover the dealkylate product. In some embodiments, the C10+ dealkylation reactor 116 may implement a steam dealkylation process may be operated at a temperature in the range of about 480° C. to about 550° C., The hydrodealkylation catalyst used in the C10+ dealkylation reactor 116 may be capable of selectively converting C10+ aromatics (such as DMEBs and tetramethylbenzenes) and hydrogen into benzene, xylene, and alkanes. In some embodiments, the hydrodealkylation catalyst may be capable of converting a significant portion and, in some embodiments, all of the C10+ aromatics to benzene, xylene, and alkanes (for example, ethane and propane) at the appropriate reaction operating conditions. It should be appreciated that one of ordinary skill in the art may select an appropriate, commercially available hydrodealkylation catalyst for performing the dealkylation portion of the process without undue or excessive experimentation. As will be appreciated, such parameters in selecting the physical, selectivity, and activity attributes of an appropriate hydrodealkylation catalyst may include dealkylation stage operating conditions, feed stock compositions, ratios of hydrogen to C10+ aromatics, desired conversion efficacy and efficiency, dealkylation stage residence time, and physical attributes of the dealkylation stage. In some embodiments, the catalyst used in the C10+ dealkylation reactor 116 may include a fluorinated zeolite catalyst. In some embodiments, a zeolite catalyst may include metal ions (for example, $Ni^{2+}$) incorporated into the crystalline structure of the catalyst. In some embodiments, the metal ions may include other Group 8, Group 9, and Group 10 transition metals, such as cobalt and palladium.

Production of Benzene, Para-Xylene, and Olefins

Embodiments of the disclosure may also include the production of olefins instead of alkanes by operating the C9 dealkylation reactor 110, the transalkylation/isomerization reactor 114, and the C10+ dealkylation reactor 116 in the absence of hydrogen. FIG. 2 depicts an integrated process 200 for another embodiment of the three reactor dealkylation and transalkylation system for the production of benzene and para-xylene from heavy reformate in. In the configuration depicted in FIG. 2, the reformate splitter 102, the xylene splitter 104, the para-xylene separator 106, and the toluene disproportionation unit 108 may operate in the manner described supra. In some embodiments, the process 200 may include the C9/C10+ splitter 118 downstream of the transalkylation/isomerization reactor 114. As described infra, the process 200 includes three reactors to process a reformate feed and produce benzene, para-xylene, and olefins from the reformate feed: the C9 dealkylation reactor 110, the transalkylation/isomerization reactor 114, and the C10+ dealkylation reactor 116. The process 200 may omit a PSA unit, as the C9 dealkylation reactor 110, the transalkylation/isomerization reactor 114, and the C10+ dealkylation reactor 116 are operated in the absence of hydrogen and no hydrogen recovery is performed.

As shown in FIG. 2, a feed stream 202 to the integrated process 200 may be a combined stream of reformate from a typical catalytic naphtha reformer, a recycled product stream 204 from the transalkylation/isomerization reactor and the C10+ dealkylation reactor 116. In some embodiments, the feed stream 202 may be a combined stream of pyrolysis gasoline from a steam cracking furnace and the recycled product stream 204 from the transalkylation/isomerization reactor 114 and the C10+ dealkylation reactor 116.

As shown in FIG. 2, the feed stream 202 is provided to the reformate splitter 102. The reformate splitter 102 produces product streams of benzene 206 and toluene 208 from the feed stream 202. The toluene 208 output from the reformate splitter 102 may be provided to the toluene disproportionation unit 108. In some embodiments, a portion 210 of the toluene stream 208 output from the reformate splitter 102 may be provided to the transalkylation/isomerization reactor 114, as described in the disclosure, to improve the transalkylation efficiency. The reformate splitter 102 may also remove saturated liquid hydrocarbons (for example, napthenes and paraffins). The C8+ aromatics stream 212 produced by the reformate splitter 102 may be provided to the xylene splitter 104.

The xylene splitter 104 may separate C8 aromatics 214 (for example. xylenes and ethylbenzene), C9 aromatics 216, and C10+ aromatics 218 from the C8+ aromatics stream 212 received from the reformate splitter 102. As shown in FIG. 2, the C8 aromatics stream 214 may be provided to the para-xylene separator 106, the C9 aromatics stream 216 may be provided to the C9 dealkylation reactor 110, and the C10+ aromatics streams 218 may be provided to the C10+ dealkylation reactor 116.

The para-xylene separator 106 may separate and produce product streams of para-xylene 220 and para-xylene-free mixed xylenes 222 (that is, ortho- and meta-xylenes) from the C8 aromatics 214 received from the reformate splitter 102. The para-xylene-free mixed xylenes 222 produced by the para-xylene separator 106 may be provided to the transalkylation/isomerization reactor 114 for reestablishing a C8 thermodynamic equilibrium of xylene isomers and promote formation of additional para-xylene. Additionally or alternatively, a portion 226 (or, in some embodiments, all of) of the para-xylene-free mixed xylenes stream 222 may be provided to the C9 dealkylation reactor 110 for subsequent isomerization over a catalyst (for example, a narrower pore catalyst) that may be more suitable for the isomerization of xylenes.

As shown in FIG. 2, the C9 dealkylation reactor 110 may receive the C9 aromatics 216 from the xylene splitter 104 and, in the absence of hydrogen, produce product streams of toluene 228, unconverted C9 aromatics 230, and olefins 232. In some embodiments, as previously noted, the C9 dealkylation reactor 110 may receive a portion 226 (or, in some embodiments, all of) of the para-xylene-free mixed xylenes 222 output from the para-xylene separator 106. As previously noted, the C9 dealkylation reactor 110 may be configured to achieve reaction conditions sufficient to maximize the conversion of C9 aromatics such as MEBs (for example, ethyltoluenes, isobenzenes, and propylbenzenes), to toluene, benzene, and olefins. In some embodiments, the C9 dealkylation reactor 110 may be operated under the following conditions: a temperature in the range of about 200° C. to about 540° C., pressure in the range of about 10 bar to about 50 bar, and a liquid hourly velocity in the range of about 1 $hr^{-1}$ to about 20 $hr^{-1}$.

As will be appreciated, the configuration and catalyst formulation of the C9 dealkylation reactor 110 may be different when the C9 aromatics 216 are processed in the absence of hydrogen. In some embodiments, the catalysts used in the C9 dealkylation reactor 110 in the absence of hydrogen may include monofunctional catalysts. Such monofunctional catalysts may include dealkylation catalysts without a metal component in the catalyst formulation. The dealkylation catalyst used in the C9 dealkylation reactor 110 may be capable of selectively converting MEBs into toluene, benzene, and olefins. In some embodiments, the dealkylation catalyst may be capable of converting a significant portion and, in some embodiments, all of the MEBs to toluene, benzene, and olefins at the appropriate reaction operating conditions. It should be appreciated that one of ordinary skill in the art may select an appropriate, commercially available dealkylation catalyst for performing the dealkylation portion of the process without undue or excessive experimentation. As will be appreciated, such parameters in selecting the physical, selectivity, and activity attributes of an appropriate dealkylation catalyst may include dealkylation stage operating conditions, feed stock compositions, desired conversion efficacy and efficiency, dealkylation stage residence time, and physical attributes of the dealkylation stage. In some embodiments, the catalyst used in the C9 dealkylation reactor 110 may include a fluorinated zeolite catalyst.

Additionally, in such embodiments, the C9 dealkylation reactor 110 operated to produce olefins in the absence of hydrogen may be a fluid-bed reactor or a moving bed-reactor to overcome rapid catalyst deactivation due to coke deposition on the catalyst. In some embodiments, the catalysts used to conduct dealkylation in the C9 dealkylation reactor 110 may also be capable of conducting xylene isomerization in embodiments in which the portion 226 (or, in some embodiments, all of) of the para-xylene-free mixed xylenes 222 are provided to the C9 dealkylation reactor 110. The toluene stream 228 and unconverted C9 aromatics stream 230 produced by the C9 dealkylation reactor 110 may be provided to the transalkylation/isomerization reactor 114. Additionally, any benzene formed by the C9 dealkylation reactor 110 may also be provided to the transalkylation/isomerization reactor 114. The olefins stream 232 produced by the C9 dealkylation reactor 110 may be combined with other produced olefin streams and provided to other processes or systems.

The transalkylation/isomerization reactor 114 may receive the liquid effluent (that is, the toluene stream 228 and the unconverted C9 aromatics stream 230) from the C9 dealkylation reactor 110 and output product streams of BTX and C9+ aromatics 234 and olefins 236. As shown in FIG. 2, the transalkylation/isomerization reactor 114 may also receive the para-xylene-free mixed xylenes 222 produced by the para-xylene separator 106. As also shown in FIG. 1, in some embodiments, the transalkylation/isomerization reactor 114 may also receive the additional toluene stream 210 from the reformate splitter 102. In some embodiments that include the C9/C10+ splitter 118, the transalkylation/isomerization reactor 114 may also receive a recycled C9 aromatics 238 produced by the C9/C10+ splitter 118.

As previously discussed, the transalkylation/isomerization reactor 114 may be configured to maximize the transalkylation of TMB-rich C9 aromatics and toluene to produce xylenes. The transalkylation/isomerization reactor 114 may also be configured to perform isomerization of the para-xylene-free mixed xylenes 222 to reestablish the C8 aromatics thermodynamics equilibrium. As shown in FIG. 2 and by recycle stream 204, the BTX and C9+ aromatics 234 may be recycled to the reformate splitter 102 for the recovery of benzene and toluene and subsequent recovery of para-xylene via the para-xylene separator 106. The olefins stream 236 produced by the transalkylation/isomerization reactor 114 may be combined with other produced olefin streams and provided to other processes or systems. In some embodiments, the transalkylation/isomerization reactor 114 may be operated under the following conditions: a temperature in the range of about 200° C. to about 540° C., pressure in the range of about 10 bar to about 50 bar, and liquid hourly velocity in the range of about 1 $hr^{-1}$ to about 20 $hr^{-1}$.

The transalkylation catalyst used in the transalkylation/isomerization reactor 114 may be capable of selectively converting TMBs and toluene into mixed xylenes. In some embodiments, the transalkylation catalyst used in the transalkylation/isomerization reactor 114 may be capable of converting a significant portion and, in some embodiments, all, of the TMBs in C9 aromatics 230 output from the C9 dealkylation reactor 110 to mixed xylenes in the presence of appropriate reaction operating conditions. It should be appreciated that one of ordinary skill in the art may select an appropriate, commercially available transalkylation catalyst for performing the transalkylation portion of the process without undue or excessive experimentation. As will be appreciated, such parameters in selecting the physical, selectivity, and activity attributes of an appropriate transalkylation catalyst may include transalkylation operating conditions, feed stock compositions, ratios of toluene to TMBs, desired conversion efficacy and efficiency, stage residence time, and physical attributes of the second stage reaction vessel to support the conversion of TMBs and toluene to mixed xylenes using a transalkylation catalyst. In some embodiments, the catalyst used in the transalkylation/isomerization reactor 114 may include a beta zeolite having an activity promoter selected from the group consisting of silicon, phosphorus, boron, magnesium, tin, titanium, zirconium, molybdenum, germanium, indium, lanthanum, cesium, and any oxide thereof.

As shown in FIG. 2, in some embodiments, the BTX and C9+ aromatics stream 234 produced by the transalkylation/isomerization reactor 114 may be recycled to the reformate splitter 102 for the recovery of benzene and toluene and subsequent recovery of para-xylene via the para-xylene separator 106. In other embodiments, the process 200 may include may include the C9/C10+ splitter 118 downstream from the transalkylation/isomerization reactor 114. In such embodiments, the BTX and C9+ aromatics stream 235 produced by the transalkylation/isomerization reactor 114 may be provided to the C9/C10+ splitter 118. For example, in some embodiments, the C9/C10+ splitter 118 may be included when reaction conditions in the transalkylation/isomerization reactor 114 result in TMBs as the majority of C9 aromatics produced by the transalkylation/isomerization reactor 114. As previously discussed, the C9/C10+ splitter 118 may separate C9 aromatics from C10+ aromatics and produce product streams of C9 aromatics 238 and C10+ aromatics 240. The C9 aromatics stream 238 produced by the C9/C10+ splitter 118 may be recycled to the transalkylation/isomerization reactor 114, and the C10+ aromatics stream 240 produced by the C9/C10+ splitter 118 may be provided to the C10+ dealkylation reactor 116. For example, in some embodiments, the C9/C10+ splitter 118 may be included when reaction conditions in the transalkylation/isomerization reactor 114 result in TMBs as the majority of the C9 aromatics output from the transalkylation/isomerization reactor 114.

As shown in FIG. 2, the C10+ dealkylation reactor 116 may receive the C10+ aromatics stream 218 from the xylene splitter 104 and produce product streams of liquid hydrocarbons 242 and olefins 244. In alternate embodiments, the C10+ dealkylation reactor 116 may receive steam from a steam source and may implement a steam dealkylation process. In embodiments that include the C9/C10+ splitter 118, the C10+ dealkylation reactor 116 may also receive C10+ aromatics 240 from the C9/C10+ splitter. The C10+ dealkylation reactor 116 may be configured to remove alkyl groups attached to aromatic benzene rings to produce a benzene-rich product. Additionally, ethyl and propyl groups attached to the C10+ aromatic molecules may form olefins such as ethylene and propylene. The liquid hydrocarbons 242 produced by the C10+ dealkylation reactor 116 may be recycled to the reformate splitter 102, as shown by recycle stream 204. The olefins stream 244 output produced by the C10+ dealkylation reactor 116 may be combined with other produced olefin streams and provided to other processes or systems. In some embodiments, the C10+ dealkylation reactor 116 may be operated under the following conditions: temperature in the range of about 300° C. to about 450° C., pressure in the range of about 10 bar to about 40 bar, weight hour space velocity (WHSV) in the range of about 0.5 to about 3, and a hydrogen to feed stream ratio in the range of 2 to 4.

In some embodiments, the catalysts used in the C10+ dealkylation reactor 116 in the absence of hydrogen may include monofunctional catalysts. Such monofunctional catalysts may include dealkylation catalysts without a metal component in the catalyst formulation. The hydrodealkylation catalyst used in the C10+ dealkylation reactor 116 may be capable of selectively converting C10+ aromatics (such as DMEBs and tetramethylbenzenes) into benzene and xylene. Additionally, the large number of ethyl and, in smaller numbers, propyl groups attached to the C10+ aromatic molecules may easily form olefins such as ethylene and propylene when the dealkylation reaction is performed in the absence of hydrogen However, as will be appreciated, rapid catalyst deactivation may occur when the C10+ dealkylation reactor 116 is operated in the absence of hydrogen. In such embodiments, steam may be introduced to the C10+ dealkylation reactor 116, and the C10+ dealkylation reactor 116 may be configured as a fluid-bed or moving-bed catalytic reactor.

In some embodiments, the dealkylation catalyst may be capable of converting a significant portion and, in some embodiments, all of the C10+ aromatics to benzene, xylene, and olefins at the appropriate reaction operating conditions. It should be appreciated that one of ordinary skill in the art may select an appropriate, commercially available dealkylation catalyst for performing the dealkylation portion of the process without undue or excessive experimentation. As will be appreciated, such parameters in selecting the physical, selectivity, and activity attributes of an appropriate dealkylation catalyst may include dealkylation stage operating conditions, feed stock compositions, desired conversion efficacy and efficiency, dealkylation stage residence time, and physical attributes of the dealkylation stage. In some embodiments, the catalyst used in the C10+ dealkylation reactor 116 may include a fluorinated zeolite catalyst. In such embodiments, the zeolite catalyst may not include any metal ions.

Ranges may be expressed in the disclosure as from about one particular value, to about another particular value, or both. When such a range is expressed, it is to be understood that another embodiment is from the one particular value, to the other particular value, or both, along with all combinations within said range.

Further modifications and alternative embodiments of various aspects of the disclosure will be apparent to those skilled in the art in view of this description. Accordingly, this description is to be construed as illustrative only and is for the purpose of teaching those skilled in the art the general manner of carrying out the embodiments described in the disclosure. It is to be understood that the forms shown and described in the disclosure are to be taken as examples of embodiments. Elements and materials may be substituted for those illustrated and described in the disclosure, parts and processes may be reversed or omitted, and certain features may be utilized independently, all as would be apparent to one skilled in the art after having the benefit of this description. Changes may be made in the elements described in the disclosure without departing from the spirit and scope of the disclosure as described in the following claims. Headings used described in the disclosure are for organizational purposes only and are not meant to be used to limit the scope of the description.

What is claimed is:

1. A heavy reformate processing system for producing benzene and para-xylene from a heavy reformate, the heavy reformate processing system comprising:
a reformate splitter operable to receive a feed stream, the feed stream comprising heavy reformate, the reformate splitter further operable to produce benzene, toluene, and a C8+ aromatics product, the C8+ aromatics product provided to a xylene splitter;
a para-xylene separator operable to receive a C8 aromatic product from the xylene splitter and produce a first xylene product comprising para-xylene and a second xylene product comprising ortho-xylene and meta-xylene;
a first dealkylation reactor operable to receive a C10+ aromatics product from the xylene splitter and produce the first dealkylation product, the first dealkylation reactor further operable to:
produce alkanes from the C10+ aromatics product and hydrogen, or
produce olefins from the C10+ aromatic product in the absence of hydrogen;
a second dealkylation reactor operable to receive a C9 aromatics product from the xylene separator and produce a second dealkylation product, the second dealkylation reactor further operable to:
produce alkanes from the C9 aromatics product and hydrogen; or
produce olefins from the C9 aromatic product in the absence of hydrogen a transalkylation reactor operable to receive the second dealkylation product from the second dealkylation reactor and produce the transalkylation product, the transalkylation reactor further operable to:
produce alkanes from the second dealkylation product and hydrogen; or
produce olefins from the second dealkylation product in the absence of hydrogen.

2. The heavy reformate processing system of claim 1, wherein the feed stream further comprises the transalkylation product and the first dealkylation product.

3. The heavy reformate processing system of claim 1, the transalkylation reactor further operable to perform isomerization of xylene to promote the formation ofpara-xylene.

4. The heavy reformate processing system of claim 1, comprising a pressure swing adsorption (PSA) unit operable to:
receive alkanes and unreacted hydrogen from the first dealkylation reactor, the second dealkylation reactor, and the transalkylation reactor.

5. The heavy reformate processing system of claim 4, wherein the first dealkylation reactor is further operable to receive recovered hydrogen from the PSA unit.

6. The heavy reformate processing system of claim 4, wherein the transalkylation reactor is further operable to receive recovered hydrogen from the PSA unit.

7. The heavy reformate processing system of claim 1, comprising a C9/C10+ splitter downstream from the transalkylation reactor, the C9/C10+ splitter operable to receive a portion of the transalkylation product from the transalkylation reactor and produce a C9 aromatics stream and a C10+ aromatics stream.

8. The heavy reformate processing system of claim 7, wherein the transalkylation reactor is further operable to receive the C9 aromatics stream produced by the C9/C10+ splitter.

9. The heavy reformate processing system of claim 7, wherein the first dealkylation reactor is further operable to receive the C10+ aromatics stream produced by the C9/C10+ splitter.

10. The heavy reformate processing system of claim 1, wherein the transalkylation reactor is further operable to receive toluene produced by the reformate splitter.

11. The heavy reformate processing system of claim 1, wherein the second dealkylation reactor operable is further operable to receive the second xylene product comprising ortho-xylene and meta-xylene produced by the xylene splitter.

12. The heavy reformate processing system of claim 1, wherein the alkanes comprise ethane and propane.

13. The heavy reformate processing system of claim 1, wherein the olefins comprise ethylene and propylene.

14. A method for producing benzene and para-xylene from a heavy reformate, the method comprising:
receiving a feed stream at a reformate splitter, the feed stream comprising heavy reformate;
operating the reformate splitter to produce benzene, toluene, and C8+ aromatics from the feed stream;
operating a xylene splitter to receive the C8+ aromatics and produce C8 aromatics, C9 aromatics, and C10+ aromatics;
operating apara-xylene separator to receive the C8 aromatics from the xylene splitter and produce a first xylene product comprising para-xylene and a second xylene product comprising ortho-xylene and meta-xylene;
operating a first dealkylation reactor to receive the C10+ aromatics from the xylene separator and produce the first dealkylation product;
operating a second dealkylation reactor operable to receive the C9 aromatics from the xylene separator and produce a second dealkylation product; and
operating a transalkylation reactor to receive the second dealkylation product from the second dealkylation reactor and produce the transalkylation product.

15. The method of claim 14, comprising:
operating the first dealkylation reactor to produce alkanes from the C10+ aromatics product and hydrogen;
operating the second dealkylation reactor to produce alkanes from the C9 aromatics product and hydrogen; and
operating the transalkylation reactor to produce alkanes from the second dealkylation product and hydrogen.

16. The method of claim 15, wherein the alkanes comprise ethane and propane.

17. The method of claim 14, comprising operating a pressure swing adsorption (PSA) unit to receive alkanes and unreacted hydrogen from the first dealkylation reactor, the second dealkylation reactor, and the transalkylation reactor.

18. The method of claim 14, comprising operating a C9/C10+ splitter downstream from the transalkylation reactor to receive a portion of the transalkylation product from the transalkylation reactor and produce a C9 aromatics stream and a C10+ aromatics stream.

19. The method of claim 18, comprising operating the transalkylation reactor to receive the C9 aromatics stream produced by the C9/C10+ splitter.

20. The method of claim 18, comprising operating the first dealkylation reactor to receive the C10+aromatics stream produced by the C9/C10+ splitter.

21. The method of claim 14, comprising operating the second dealkylation reactor operable is further operable to receive the second xylene product comprising ortho-xylene and meta-xylene produced by the xylene splitter.

22. The method of claim 14, comprising:
operating the first dealkylation reactor to produce olefins from the C10+ aromatic product in the absence of hydrogen;
operating the second dealkylation reactor to produce olefins from the C9 aromatic product in the absence of hydrogen; and
operating the transalkylation reactor to produce olefins from the second dealkylation product in the absence of hydrogen.

23. The method of claim 22, wherein the olefins comprise ethylene and propylene.

24. The method of claim 14, comprising operating transalkylation reactor to perform isomerization of xylene to promote the formation of para-xylene.

* * * * *

UNITED STATES PATENT AND TRADEMARK OFFICE
CERTIFICATE OF CORRECTION

| | |
|---|---|
| PATENT NO. | : 10,173,950 B2 |
| APPLICATION NO. | : 15/826117 |
| DATED | : January 8, 2019 |
| INVENTOR(S) | : Abudawoud et al. |

It is certified that error appears in the above-identified patent and that said Letters Patent is hereby corrected as shown below:

On the Title Page

Under "Related U.S. Application Data" it should read:
-- Provisional application No. 62/442,124, filed on Jan. 4, 2017. --

In the Claims

In Column 17, Claim 3, Line 45 should read:
-- of xylene to promote the formation of para-xylene. --

Signed and Sealed this
Second Day of April, 2019

Andrei Iancu
*Director of the United States Patent and Trademark Office*